(12) United States Patent
DeGroot et al.

(10) Patent No.: US 7,650,188 B2
(45) Date of Patent: Jan. 19, 2010

(54) MEANS FOR AUGMENTING MEDICAL ELECTRICAL SYSTEMS

(75) Inventors: Paul J. DeGroot, Brooklyn Park, MN (US); Karel F. A. A. Smits, Munstergeleen (NL)

(73) Assignee: Medtronic, Inc., Minneapolis, MN (US)

( * ) Notice: Subject to any disclaimer, the term of this patent is extended or adjusted under 35 U.S.C. 154(b) by 643 days.

(21) Appl. No.: 10/914,369

(22) Filed: Aug. 9, 2004

(65) Prior Publication Data

US 2006/0030224 A1 Feb. 9, 2006

(51) Int. Cl.
*A61N 1/362* (2006.01)

(52) U.S. Cl. .......................................... 607/37; 607/36

(58) Field of Classification Search .............. 607/36–38
See application file for complete search history.

(56) References Cited

U.S. PATENT DOCUMENTS

| | | | | |
|---|---|---|---|---|
| 3,735,766 | A | * | 5/1973 | Bowers et al. ................ 607/36 |
| 5,376,103 | A | * | 12/1994 | Anderson et al. .............. 607/5 |
| 5,385,574 | A | * | 1/1995 | Hauser et al. .................. 607/4 |
| 5,413,595 | A | * | 5/1995 | Stutz, Jr. ...................... 607/37 |
| 5,439,484 | A | * | 8/1995 | Mehra ........................... 607/5 |
| 5,531,766 | A | * | 7/1996 | Kroll et al. .................... 607/5 |
| 5,620,477 | A | * | 4/1997 | Pless et al. ................... 607/37 |
| 5,658,321 | A | * | 8/1997 | Fayram et al. ............... 607/36 |
| 6,080,188 | A | * | 6/2000 | Rowley et al. ............... 607/37 |
| 6,198,969 | B1 | | 3/2001 | Kuzma ......................... 607/37 |
| 6,327,502 | B1 | | 12/2001 | Johansson et al. ............ 607/36 |
| 7,062,329 | B2 | * | 6/2006 | Ostroff ......................... 607/37 |

* cited by examiner

*Primary Examiner*—George R Evanisko (57) ABSTRACT

A medical electrical system includes a device including a connector port and an external electrically active surface and an auxiliary lead including a supplemental electrode and a connector end. The external electrically active surface of the device is adapted to receive the auxiliary lead connector end, thereby electrically coupling the supplemental electrode to the device via contact between the connector end and the external surface.

11 Claims, 7 Drawing Sheets

MEANS FOR AUGMENTING MEDICAL ELECTRICAL SYSTEMS

TECHNICAL FIELD

The present invention relates to medical electrical systems and more particularly to means for augmenting medical electrical systems.

BACKGROUND

In the field of medical electrical systems, it is often desirable to utilize a minimum number of implanted medical electrical leads, each including as many electrodes and/or physiological sensors as are feasible. It is further desirable to reduce the number of connections between each lead and an implanted device in order to reduce bulk in a subcutaneous pocket where the device resides.

Medical electrical lead connectors and the mating connector ports of devices have been standardized in the industry; examples of standards for cardiac therapy include the IS-1 standard, for low voltage applications, i.e. pacing, and the DF-1 standard, for high-voltage applications, i.e. defibrillation. Other contemplated standards define connections for both high-voltage and low-voltage with a single device connector port and a single lead connector in order to achieve a lower profile system.

Clinical experience has shown that, in some patients, an acceptable defibrillation threshold cannot be reached using two high-voltage electrodes located on a single lead. In other patients, a chronic energy requirement for effective defibrillation may increase due to worsening heart condition or a change in medication. For these patients, it becomes necessary to implant, either at the time of original device implantation or after that time, another defibrillation electrode in order to create an effective vector for the delivery of defibrillation energy.

Furthermore it is contemplated that two low voltage electrodes located on a single lead may not meet the long term therapeutic goals for an implanted system, for example to provide cardiac resynchronization, and that, in these cases, an additional pacing electrode should be added to the system.

For the aforementioned cases, along with others in the broader field of medical electrical systems, it is desirable to provide means for augmenting a medical electrical system without adding an additional device connector port.

BRIEF DESCRIPTION OF THE DRAWINGS

The following drawings are illustrative of particular embodiments of the invention and therefore do not limit its scope, but are presented to assist in providing a proper understanding of the invention. The drawings are not to scale (unless so stated) and are intended for use in conjunction with the explanations in the following detailed description. The present invention will hereinafter be described in conjunction with the appended drawings, wherein like numerals denote like elements, and.

DETAILED DESCRIPTION

The following detailed description is exemplary in nature and is not intended to limit the scope, applicability, or configuration of the invention in any way. Rather, the following description provides a practical illustration for implementing exemplary embodiments of the invention.

Figure 1:
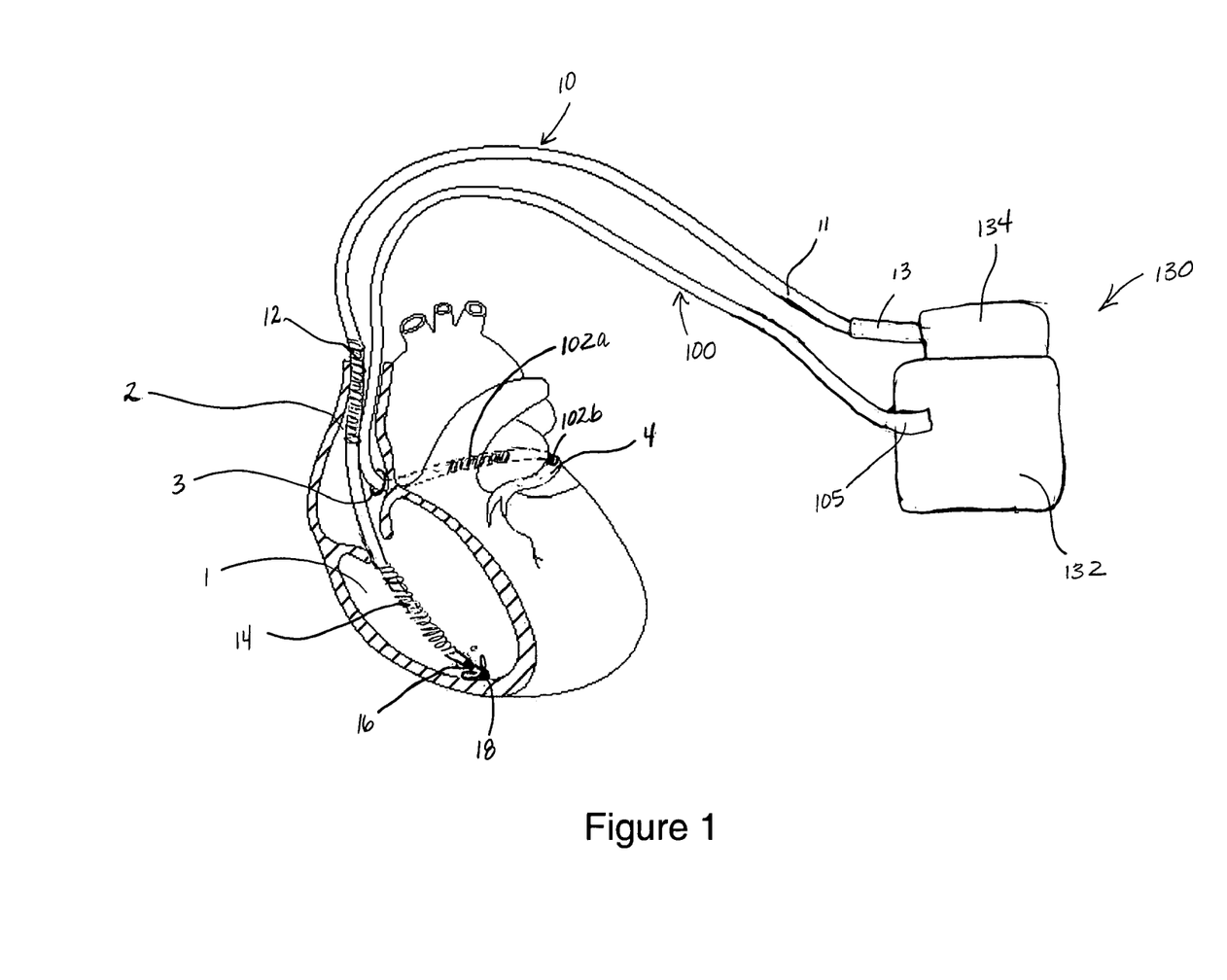
FIG. 1 is a schematic showing an implanted medical electrical system according to one embodiment of the present invention.

FIG. 1 is a schematic showing an implanted medical electrical system according to one embodiment of the present invention. FIG. 1 illustrates the system including a medical electrical lead 10 and an auxiliary medical electrical lead 100, each coupled to a pulse generator or device 130, which includes a hermetically sealed enclosure or housing 132, containing a battery and electronic circuitry (not shown), and a connector module 134 fixedly attached to housing 132. According to the illustrated embodiments, lead 10 is coupled to device 130 via a connector port 43 (FIG. 4A) formed in connector module 134, and auxiliary lead 100 is directly connected to housing 132 by means of a connector end 105. FIG. 1 further illustrates each of leads 10 and 100 extending from device 130 into a heart of a patient; lead 10 includes a pair of electrodes 16 and 18 for pacing and sensing, implanted in a apex of a right ventricle 1, a first defibrillation or high voltage electrode 14, also within right ventricle 1, and a second defibrillation or high voltage electrode 12 positioned in a superior vena cava, while auxiliary lead 100 includes a supplemental electrode which may be either a high voltage electrode 102a or a low voltage electrode 102b implanted within a coronary vasculature of the heart, having been passed through a coronary sinus ostium 3.

According to the illustrated embodiment, lead 10 has been implanted to provide for right ventricular pacing and sensing, via electrodes 18 and 16, and cardiac defibrillation, via high voltage electrodes 12 and 14 and, in some cases, in conjunction with housing 132, which may further act as a high voltage electrode (known in the art as an "active can"); a defibrillation shocking vector may be formed between housing 132 and electrode 12, having a common electrical polarity, and electrode 14 having an opposite electrical polarity. According to one embodiment illustrated by FIG. 1, auxiliary lead 100 includes high voltage electrode 102a as the supplemental electrode, which has been positioned in a coronary sinus to augment the shocking vector, having a common polarity with housing 132 and electrode 12; according to another embodiment shown by FIG. 1, auxiliary lead 100 includes low voltage electrode 102b, having a common polarity with housing 132, as the supplemental electrode, which has been positioned in a cardiac vein 4 in order to pace the left ventricle in conjunction with electrode 16 of lead 10. According to the former embodiment, it would have been found, via defibrillation threshold testing at the time of implant or by observation of system performance after implant, that an acceptable defibrillation threshold will require that a supplemental defibrillation electrode, for example electrode 102a, be implanted to augment the shocking vector. According to the latter embodiment it would have been found, via observation of system performance after implant, for example by analyzing electrocardiograms sensed by electrodes of lead 10 or by monitoring cardiac pump performance via echocardiography, that the heart's hemodynamic performance could be improved with cardiac resynchronization therapy, which will require that a supplemental pacing electrode, for example electrode 102b, be implanted to pace the left ventricle.

Figure 2:
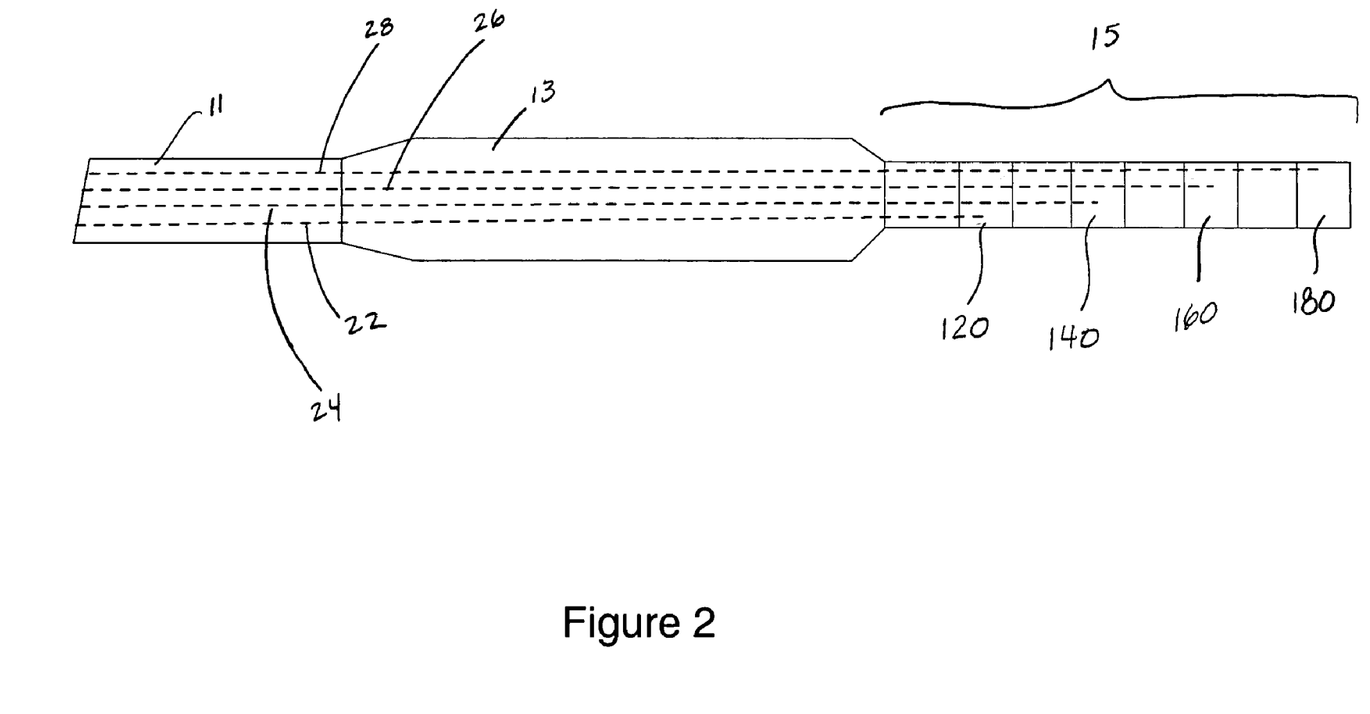
FIG. 2 is a plan view of a connector portion of a lead included in the system illustrated in FIG. 1.

FIG. 2 is a plan view of a connector portion of lead 10. FIGS. 1 and 2 illustrate lead 10 including a lead body 11 coupled to a connector terminal 15 by means of a connector sleeve 13; connector terminal 15 is inserted into port 43 of module 134 to make electrical connections between device 130 and electrodes 12, 14, 16 and 18. FIG. 2 further illustrates, with dashed lines, four conductors 22, 24, 26 and 28 electrically coupled to connector contacts 120, 140, 160 and 180 respectively; conductors 22, 24, 26 and 28 extend from connector 15 through lead body 11 to couple connector contacts 120, 140, 160 and 180 with electrodes 12, 14, 16 and 18, respectively. Materials and methods that may be employed to construct lead 10 are well known to those skilled in the art.

Figure 3A:
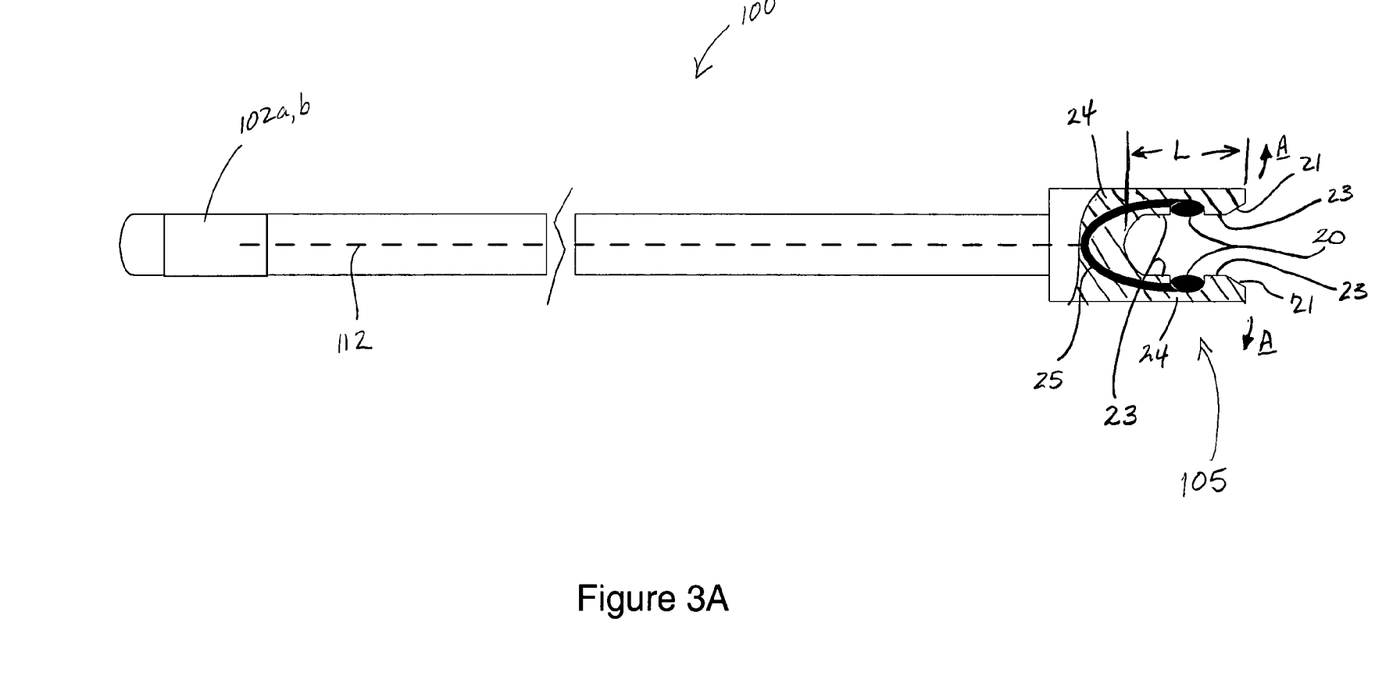
FIG. 3A is a plan view with partial section of an auxiliary lead included in the system illustrated in FIG. 1 according to some embodiments of the present invention.

FIG. 3A is a plan view with partial section of auxiliary lead 100 according to some embodiments of the present invention. In FIG. 3A the supplemental electrode is illustrated as a generic electrode which may be either high voltage supplemental electrode 102a or low voltage supplemental electrode 102b as previously described. High voltage supplemental electrode 102a may include an elongate coiled or braided wire coupled to conductor 112 or may be an exposed elongate portion of conductor 112. FIG. 3A further illustrates an insulated conductor 112 electrically coupling supplemental electrode 102a,b to contact surfaces 20 of connector end 105, and contact surfaces 20 terminating ends of a spring clamp structure 25, for example formed of stainless steel, encased within an insulative connector body 24, for example formed of silicone rubber; as illustrated in FIG. 1, connector end 105 clamps about opposite sides of electrically active surface of housing 132 thereby electrically coupling contact surfaces 20 thereto.

According to the embodiment illustrated in FIG. 3A, clamp extensions of connector end 105 include chamfered ends 21, to facilitate opening of the extensions per arrows A when connector is pushed against a side of housing 134, and internal surfaces 23 surrounding contact surfaces 20, which may form a seal preventing fluid ingress between contact surfaces 20 and housing 132 when connector is clamped onto housing 132. Although contact surfaces 20 are illustrated on each extension of connector end 105, it should be noted that a single contact surface is within the scope of the present invention. State of the art device housings, for example those formed of titanium, may be employed by embodiments of the present invention and contact surfaces 20 may be formed of a conductive metal such as titanium or stainless steel.

Figures 3B, 3C:
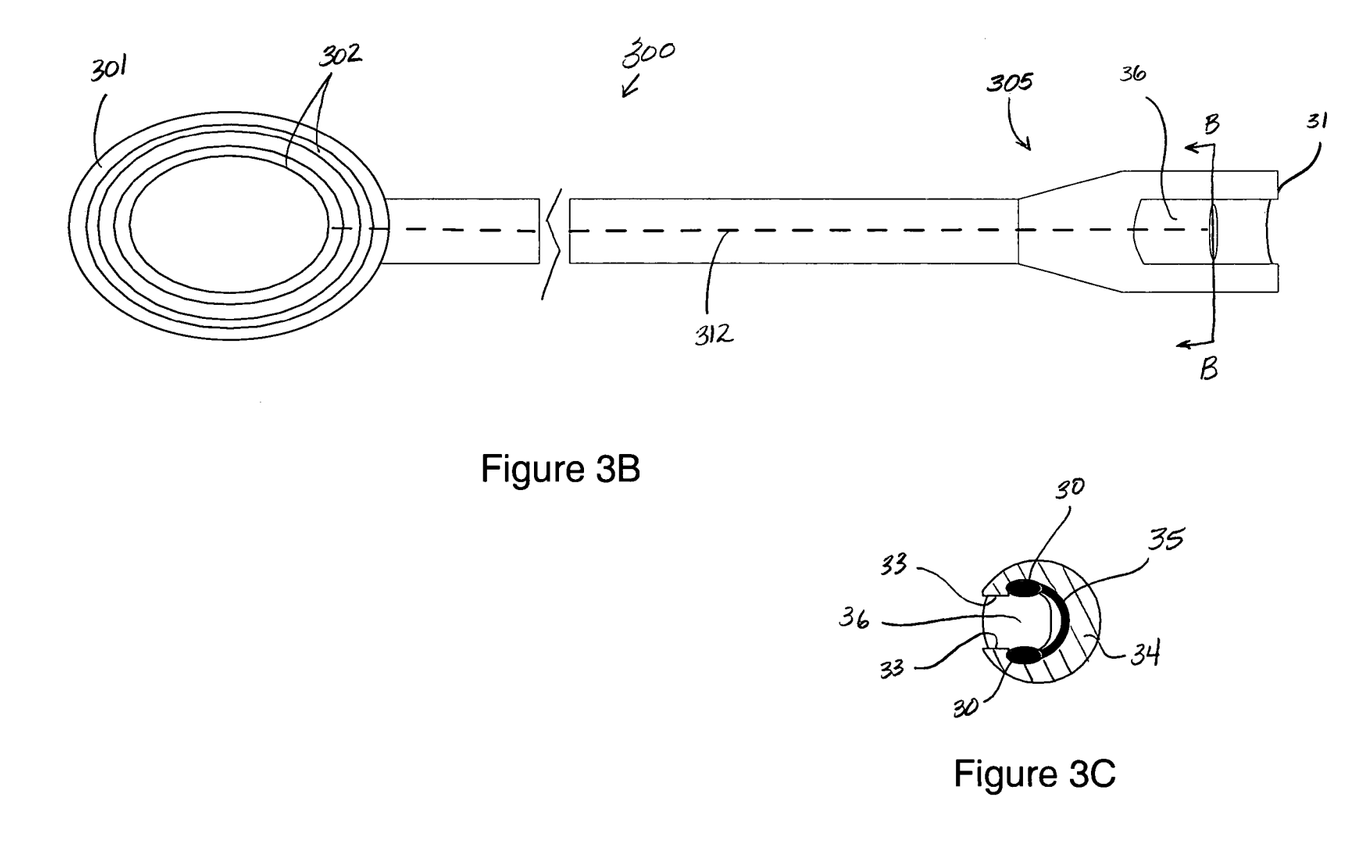
FIG. 3B is a plan view of an auxiliary lead according to an alternate set of embodiments of the present invention.
FIG. 3C is a section view, taken through section line B-B shown in FIG. 3B, according to one embodiment.

FIG. 3B is a plan view of an auxiliary lead 300 according to another embodiment of the present invention. FIG. 3B illustrates lead 300 including a supplemental high voltage electrode 302 mounted in a patch area 301 terminating a distal end of the lead; construction of such patch electrodes are well known to those skilled in the art and, according to embodiments of the present invention, such electrodes may be positioned either on an epicardial surface of a heart or in a subcutaneous region, for example a precordial region, to augment a shocking vector formed by electrodes 12 and 14 (FIG. 1). Other types of high voltage electrode configurations, for example array or finger electrodes known to those skilled in the art, are suitable alternatives for a supplemental electrode.

FIG. 3B further illustrates an insulated conductor 312 electrically coupling supplemental electrode 302 to a connector end 305 including at least one contact surface, examples of which will be described in conjunction with FIGS. 3C-D, within a cavity 36 which is adapted to connect with an external electrically active surface of a device, for example housing 132.

Figure 4A:
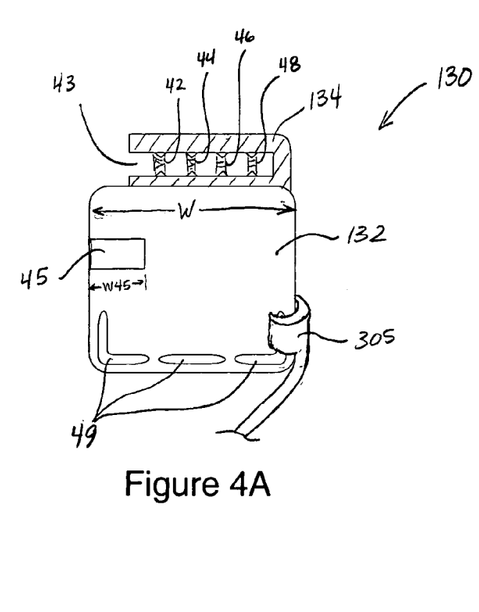
FIG. 4A is a plan view with partial section of a device and a portion of the auxiliary lead illustrated in FIGS. 3B-C according to some embodiments of the present invention.

FIG. 3C is a section view taken through section line B-B shown in FIG. 3B and illustrates connector end 305 including contact surfaces 30 terminating ends of a spring clamp structure 35, for example formed of stainless steel, encased within an insulative connector body 34, for example formed of silicone rubber, that forms cavity 36. FIG. 4A illustrates connector end 305 coupled to housing 132 such that surfaces 30 are electrically connected with housing 132. FIG. 3C further illustrates surfaces 33, which may form a seal preventing fluid ingress between contact surfaces 30 and an external electrically active surface of a device to which connector end 305 is coupled; an additional sealing surface may be formed within a proximal end 31 (FIG. 3B) of connector end 305. Although contact surfaces 30 are illustrated on opposing sides of cavity 36, it should be noted that a single contact surface is within the scope of the present invention and a position of the contact surface may be any where about the circumference of cavity 36. Contact surfaces 30 may be formed of a conductive metal such as titanium or stainless steel.

Figure 3D:
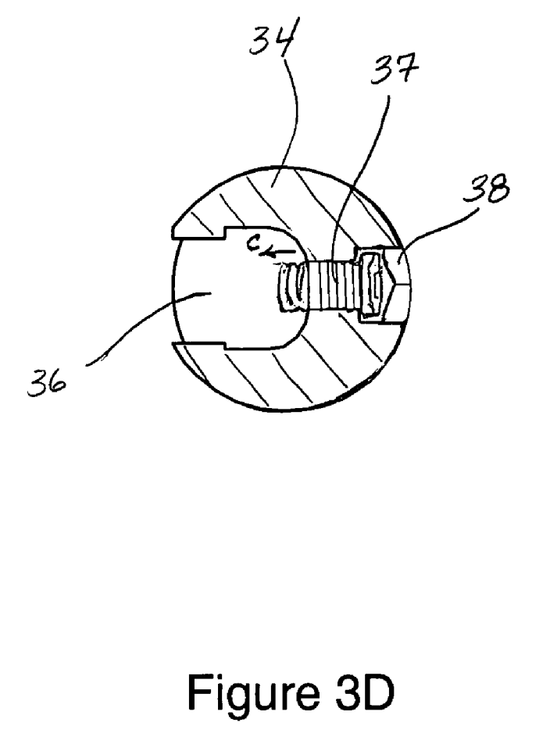
FIG. 3D is a section view, taken through line B-B shown in FIG. 3B, according to another embodiment.

FIG. 3D is a section view, taken through line B-B shown in FIG. 3B, according to another embodiment. FIG. 3D illustrates a conductive screw bolt 37 mounted within body 34 of connector end 305 and sealed from an external surface of body 34 by a grommet 38, which may be pierced by a wrench tool adapted to advance screw 37 per arrow C. According to the illustrated embodiment, screw 37 forms an electrical contact with an external electrically active surface of a device, having been screwed into a mating receptacle of the device, for example receptacle 139 of a device 135 illustrated in FIG. 4B, which is encompassed by cavity 36 of connector end 305. According to alternate embodiments, screw 37 is employed primarily to secure connector end 305 to an electrically active surface and connector end 305 also includes contact surfaces, for example surfaces 30 as illustrated in FIG. 3C, for electrical coupling with the electrically active surface. According to yet another embodiment, screw 37 is employed primarily for electrical coupling not requiring a mating receptacle and other means are employed to secure connector end 305 to an electrically active surface.

FIG. 4A is a plan view with partial section of device 130 and a portion of auxiliary lead 300 according to some embodiments of the present invention. FIG. 4A illustrates connector module 134 including four internal contacts 42, 44, 46 and 48 positioned to electrically couple with connector contacts 120, 140, 160 and 180 of connector terminal 15 (FIG. 2) when connector terminal 15 is fully inserted within connector bore 43. Each of internal contacts 42, 44, 46 and 48 may be formed as spring contacts, for example multi-beam, or as setscrew contacts, both of which are well known to those skilled in the art along with materials and methods for device connector module construction and assembly as a whole.

FIG. 4A further illustrates housing 132 including a recessed surface 45 adapted for receiving connector end 105 of lead 100 (FIGS. 1 and 3A); a width W45 of recessed surface 45 may correspond to a length L of clamp extensions of connector end 105 illustrated in FIG. 3A. According to an alternate embodiment length L of clamp extensions may correspond to a width W of housing 132 and recessed surface 45 may likewise extend across width W so that W45 is approximately equal to W, however, embodiments of the present invention need not include recessed surface 45 at all no matter what length L is. Furthermore, as can be seen in FIG. 4A, an alternate connection to the external electrically active surface of device 130, formed by housing 132, may be made with connector end 305 of lead 300, which was described in conjunction with FIGS. 3B-C. It should be noted that an entirety of the external surface of housing 132 may be electrically active for connection with connector ends of auxiliary leads or that just a portion of the external surface of housing 132, for example recessed surface 45, be active for connection.

According to another embodiment illustrated by FIG. 4A, one or more features 49 are formed on an exterior surface of housing 132 to provide a 'snap' fit, and thus additional stability of connection, for either type of connector end, connector end 305 or connector end 105; such features 49 may be either protrusions or recesses and may be arranged in any manner according to a specific geometry of a connector end to prevent both translation and rotation, or one or the other, of the connector end when coupled to housing 132.

Figure 4B:
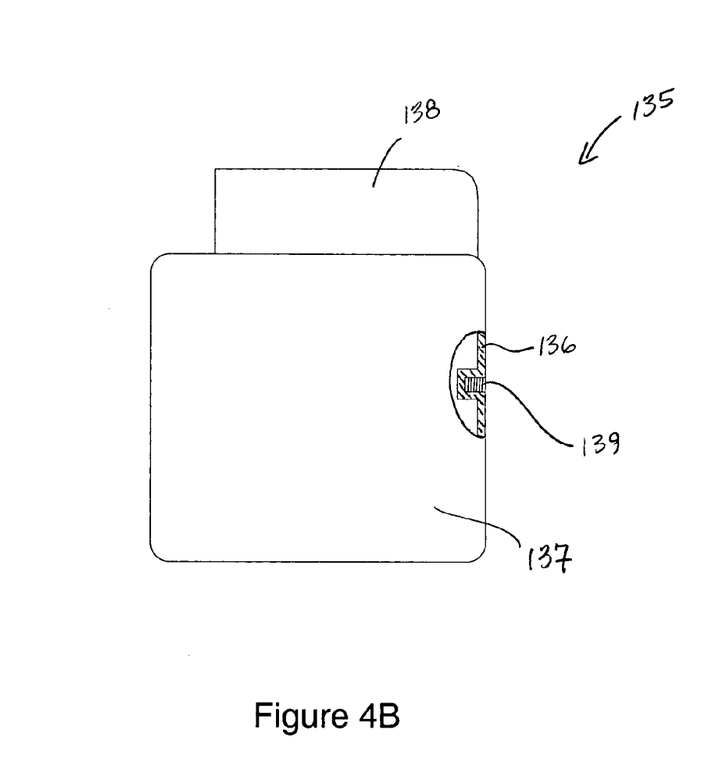
FIG. 4B is a plan view with partial section of a device adapted to mate with the auxiliary lead connector illustrated in FIG. 3D.

FIG. 4B is a plan view with partial section of device 135 adapted to mate with the auxiliary lead connector illustrated in FIG. 3D. FIG. 4B illustrates device 135 including a connector module 138 mounted on a housing 137, formed in part by a sidewall 136 having an electrically active surface in which receptacle 139 is formed. As previously described in conjunction with FIG. 3D, receptacle 139 mates with screw 37 of connector end 305 (FIG. 3B) to electrically couple electrode 302 to the electrically active surface of housing 137. Device 135 may further include a dummy screw mated with receptacle 139 or some type of covering formed over receptacle 139 to protect receptacle 139 from an implant environment that may, for example result in tissue ingrowth and or corrosion, before a mating screw bolt of a connector is coupled thereto.

Figure 4C:
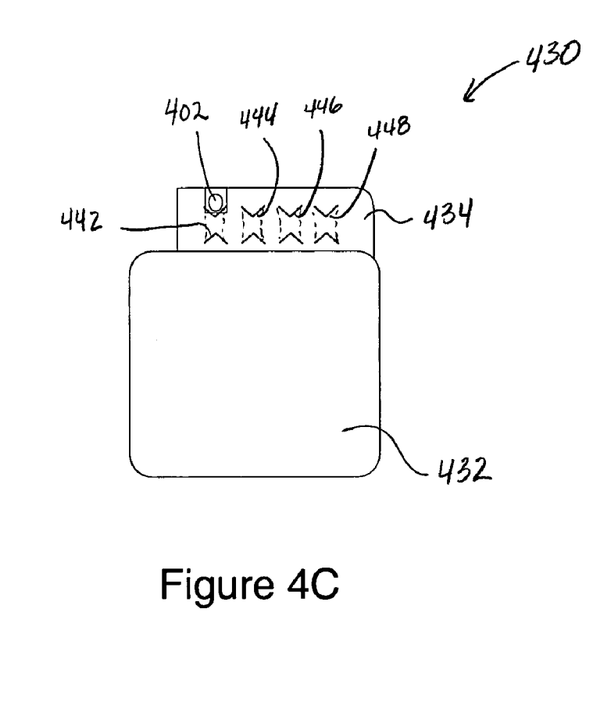
FIG. 4C is a plan view of a device according to another embodiment of the present invention.

FIG. 4C is a plan view of a device 430 according to another embodiment of the present invention. FIG. 4C illustrates device 430 including a housing 432 and a connector module 434 containing internal connector contacts 442, 444, 446 and 448, similar to device 130; however, an external electrically active surface of device 430, formed as a contact pad 402, is mounted on an outer surface of connector module 434 and electrically coupled to internal contact 442. As is well known to those skilled in the art, the body of connector module 434 is formed of an insulative material, for example polyurethane, to electrically isolate contacts 442, 444, 446 and 448 from the external implant environment and from one another. According to some embodiments of the present invention, auxiliary lead connector ends, for example end 105 or 305, are coupled to contact pad 402 in order to augment a medical electrical system with a supplemental electrode, for example electrode 102a,b or 302, as previously described. It should be noted that contact pad 402 may be electrically coupled to any of internal contacts 442, 444, 446 and 448, or to none, being electrically independent of each, and located anywhere upon external surface of connector module 430 or even on housing 432. Referring back to FIG. 4B, further alternate embodiments of the present invention include threaded recess 139 mounted on header 138 and being electrically coupled to one or more internal contacts, for example as contact pad 402 is coupled to internal contact 442.

Figure 4D:
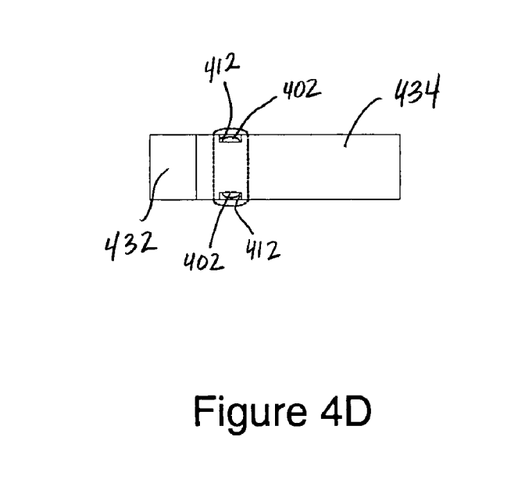
FIG. 4D is a top view of the device shown in FIG. 4C.

FIG. 4D is a top view of device 430 showing contact pad 402 as a pair on either side of connector module 434, according to one embodiment, and an optional covering 422, shown with dashed lines, for contact pads 402. According to the illustrated embodiment covering 412 wraps over a top of connector module 434 and extends down sides to cover contact pads 402 thereby isolating contact pads 402 from the implant environment prior to addition of an auxiliary lead to the system, at which time covering 412 could be peeled off from module 434, or pierced through, so that a connector end contact of the auxiliary lead may make electrical contact with contact pads 402. According to alternate embodiments, contact pads 402 include grommet seal coverings similar to those known in the art for sealing setscrew ports.

What is claimed is:

1. A medical device, comprising:
    a housing having an outer surface and a recessed area of the outer surface;
    electrical circuitry within the housing;
    a header mounted to the housing and having a connector port including an internal electrical contact, the connector port adapted to receive a connector terminal of a first medical electrical lead having an electrode, thereby electrically coupling the electrode of the first medical lead to the electrical circuitry of the medical device via contact between the connector terminal and the internal contact of the header connector port;
    an auxiliary medical electrical lead having a connector end, a supplemental electrode, and a conductor connecting the end to the electrode; and
    an external electrically conductive surface on the housing mechanically and electrically attached to the connector end of the auxiliary medical electrical lead and thereby electrically couple the supplemental electrode of the auxiliary lead to the electrical circuitry of the medical device via contact between the connector end and the external electrically conductive surface on the housing, the connector end of the auxiliary lead having a clamp structure having chamfered ends, wherein the external electrically conductive surface is only positioned in the recessed area of the outer surface.

2. The device of claim 1, wherein the connector port further includes a second internal electrical contact to electrically couple a second electrode of the lead to the medical device via contact between the connector terminal and the second internal contact.

3. The device of claim 2, wherein the external electrically active surface is electrically coupled to the second internal electrical contact.

4. The device of claim 1, wherein the connector port further includes additional internal electrical contacts to electrically couple additional electrodes of the lead to the medical device via contact between the connector terminal and the additional internal contacts.

5. The device of claim 4, wherein the external electrically active surface is electrically coupled to at least one of the additional internal contacts.

6. The medical device of claim 1, wherein the supplemental electrode is adapted for pacing.

7. The medical device of claim 1, wherein the supplemental electrode is adapted for defibrillation.

8. The medical device of claim 1 wherein the supplemental electrode is adapted for sensing.

9. The medical device of claim 1, wherein the supplemental electrode is an only electrode of the auxiliary lead.

10. The medical device of claim 1, wherein the supplemental electrode is formed as an elongate coil or braid.

11. The medical device of claim 1, wherein the electrical connector further includes one or more features to provide additional stability of connection when the connector is connected to the electrically active surface.

* * * * *

UNITED STATES PATENT AND TRADEMARK OFFICE
CERTIFICATE OF CORRECTION

| | |
|---|---|
| PATENT NO. | : 7,650,188 B2 |
| APPLICATION NO. | : 10/914369 |
| DATED | : January 19, 2010 |
| INVENTOR(S) | : DeGroot et al. |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 870 days.

Signed and Sealed this

Twenty-third Day of November, 2010

David J. Kappos
*Director of the United States Patent and Trademark Office*